United States Patent
Kendrup et al.

(10) Patent No.: US 6,974,591 B2
(45) Date of Patent: Dec. 13, 2005

(54) METHOD FOR PRODUCING A CONTROLLED-RELEASE PREPARATION

(75) Inventors: John Kendrup, Oxie (SE); Peter Fyhr, Bjärred (SE)

(73) Assignee: Watson Laboratories, Inc., Salt Lake City, UT (US)

( * ) Notice: Subject to any disclaimer, the term of this patent is extended or adjusted under 35 U.S.C. 154(b) by 0 days.

(21) Appl. No.: 09/819,813

(22) Filed: Mar. 29, 2001

(65) Prior Publication Data

US 2001/0038853 A1 Nov. 8, 2001

(30) Foreign Application Priority Data

Mar. 31, 2000 (SE) .................................. 0001151

(51) Int. Cl.$^7$ ............................. A61K 9/32; A61K 9/36; A61K 9/44; A61K 9/22
(52) U.S. Cl. ....................... 424/473; 424/474; 424/475; 424/479; 424/480; 424/482; 424/468; 514/772.3; 514/777; 514/781
(58) Field of Search .................................. 424/463, 468, 424/472, 473, 474, 475, 479, 480, 482, 486, 464

(56) References Cited

U.S. PATENT DOCUMENTS

| | | | |
|---|---|---|---|
| 4,557,925 A | 12/1985 | Lindahl et al. |
| 4,629,619 A | 12/1986 | Lindahl et al. |
| 5,376,383 A | 12/1994 | Alberts et al. |
| 5,472,712 A | 12/1995 | Oshlack et al. |
| 5,639,476 A | 6/1997 | Oshlack et al. |
| 6,024,982 A | 2/2000 | Oshlack et al. |

*Primary Examiner*—James M. Spear
(74) *Attorney, Agent, or Firm*—Thorpe North & Western, LLP

(57) ABSTRACT

The invention concerns a method for producing a controlled-release pharmaceutical preparation with a particle-containing coating, the coating being derived from an aqueous dispersion of a film-forming water insoluble polymer and a water soluble pore-forming agent. By suspending, instead of dissolving, the pore-forming agent, the resulting coating will contain particles of the pore-formers with a predetermined size that creates, when disintegrated or dissolved in the body fluid, canals or a network of pores through the polymer film. Due to this network, the film will get a good mechanical stability and are left intact after the release of the drug.

23 Claims, No Drawings

METHOD FOR PRODUCING A CONTROLLED-RELEASE PREPARATION

FIELD OF THE INVENTION

The present invention concerns a method for producing a pharmaceutical preparation. Specifically the invention concerns a method for producing a controlled-release pharmaceutical preparation with a particle-containing coating. The invention also concerns new pharmaceutical preparations.

BACKGROUND OF THE INVENTION

Many polymers are used as coatings in controlled release oral pharmaceutical preparations. These polymers are essentially water-insoluble and have consequently low permeability towards water and drugs. If the drug is very soluble and surface of the preparation is large, as in e.g. pellets, low permeability is desired. If the drug is moderately soluble or the surface of the preparation is small, as in e.g. tablets, the permeability of the coating has to be increased.

One method of increasing the permeability of the polymer is disclosed in the U.S. Pat. No. 4,629,619. According to this patent the permeability is increased by including water soluble particles in the coating. When the preparation is subsequently swallowed by a patient and contacted with the GI juices, the water soluble particles dissolve and form pores or channels in the coating through which pores or channels the drug is released from the preparation. The coating including these water soluble pore-forming particles is obtained by a method according to which the water-soluble particles are suspended in an organic solvent. Medical preparations developed according to this patent are currently used and well accepted by the patients. A disadvantage is however the necessity to use organic solvents.

Another method of increasing the permeability is disclosed in the U.S. Pat. Nos. 5,472,712 and 5,639,476. According to these two patents the permeability of the polymer is increased by including a water-soluble material in the polymer. The coating including the water soluble material is obtained by dissolving the water soluble material in the aqueous dispersion of a film-forming polymer. When such a preparation is subsequently swallowed and contacted with the GI juices the water soluble material dissolves and make the polymer coating micro-porous and increase the release rate of the drug through the coating. The sizes of the micro-pores correspond to those of the dissolved molecules. An advantage with medical preparations prepared according to these two patents is that they may be prepared without organic solvent. A disadvantage is that the mechanical strength of the coating is poor, when the permeability is increased to an acceptable level for moderately soluble drugs, especially for tablets. Another disadvantage is that the size of the pores is not controlled which means e.g. that it is difficult to obtain reproducible products.

The permeability increasing or pore-forming agents used according to the two above methods may be identical chemically but the physical state of these agents in the coating solution is different.

OBJECT OF THE INVENTION

An object of the present invention is therefore to accomplish a method for producing a controlled-release pharmaceutical preparation having the same effective release rate and mechanical strength as the one described in U.S. Pat No. 4,557,925 while avoiding the use of organic solvents and the problems arising by using the method according to U.S. Pat. Nos. 5,472,712 and 5,639,476.

SUMMARY OF THE INVENTION

This object as well as other objects that will be apparent from the description below, have now been obtained according to the present invention by providing a method for producing an essentially zero order, controlled-release pharmaceutical preparation with a particle containing coating according to claim 1.

This method comprises the steps of:

preparing a drug-containing solid core;

suspending a pore-forming agent having a balanced solubility in an aqueous dispersion of a film-forming, water insoluble polymer in order to form a coating suspension having a predetermined amount of solid particles of the pore-forming agent suspended therein;

coating the solid core with the obtained suspension; and drying the coated tablet.

By a careful selection of the type, amount and particle size of the pore-forming agent, the coating of the final tablet will contain comparatively large particles of the pore-formers. When the tablet is then contacted with the GI juices of a patient, these particles dissolve and create a network of canals or pores of a predetermined size in the polymer coating and the drug is released through these pores or canals. Due to this network the coating will get good mechanical stability and the polymer film will be left intact after the release of the drug.

A predetermined release rate may be obtained by selecting the above parameters of the pore-forming agent in combination with type and amount of film forming polymer. The coatings thus prepared have a good mechanical stability and are left intact after the release of the drug and the pore-forming agent.

The problem to be solved by the present invention is thus to find a pore-creating agent or pore-former combining the two seemingly non compatible properties of being, on one hand sufficiently insoluble in the aqueous coating dispersion, and on the other hand sufficiently soluble in the aqueous GI juices. In this context this feature is referred to as "balanced solubility".

DETAILED DESCRIPTION OF THE INVENTION

The critical pore-forming agent must be a pharmaceutically acceptable substance that can be added to the aqueous dispersion of the film-forming polymer without being completely dissolved. Important factors for the pore-forming agent are its solubility and mean particle size. The solubility of the pore-forming agent is below 200 mg/ml in the coating solution at 25° C. Preferably the solubility is below 100 mg/ml, more preferably below 50 and most preferably below 30 mg/ml.

The mean particle size of the pore-forming agent when added to the coating solution is 0.1–500 µm, preferably 0.5–100 µm and most preferably 1.0–25 µm.

If larger particles are used it will be difficult to get reproducible preparations and if smaller particles are used manufacturing problems are expected.

The predetermined amount of solid particles of the pore-forming agent in the coating solution is selected by the man skilled in the art in view of the specific drug and polymer used and the desired release rate.

In a preferred embodiment of the invention the pore-forming agent is selected from the group consisting of potassium hydrogen tartrate (potassium bitartrate), creatine, aspartic acid, glutamic acid and inosine.

Other preferred pore-forming agents are chitosan and poly(butyl methacrylate, (2-dimethyl aminoethyl) methacrylate, methyl methacrylate) 1:2:1.

Other pore-forming agents which may be used selected from a group consisting of potassium salts, calcium salts, magnesium salts, amino acids, week acids, carbohydrates, polymers with amino and/or acid functions. Examples are aspargine, glutamine, leucin, neroleucine, isoleucine, magnesium citrate, magnesium phosphate, magnesium carbonate, magnesium hydroxide, magnesium oxide or a composition wherein at least one component is selected from one of these substances.

The pore-former can also be a composition wherein at least one of the components is selected from one of these groups.

The film-forming polymer according to the present invention could be any pharmaceutically acceptable water insoluble or essentially insoluble polymer, block- or co-polymer that can be dispersed in an aqueous solution. Example of such polymers are polymers selected from the groups consisting of cellulose esters, acrylic polymers, polyvinyl acetates, polyvinyl chlorides or a composition wherein at least one component is selected from one of the groups.

Preferred substances are polyvinylacetate, polymethylmetacrylate or a terpolymer of vinylchloride, vinylalcohol and vinylacetate. Commercialy available latexes, pseudolatexes and polymer emulsions are also possible to use for the coating.

Other preferred coating polymers are ethylcellulose, celluloseacetate, celluloseacetatebutyrate, celluloseacetatepropionate, nitrocellulose, polymethylmetacrylate, poly(ethylacrylate, methylmetacrylate), polyvinylacetate, polyvinylchloride, polyethylene, polyisobutylene, poly(ethylacrylate, methylmetacrylate, trimethylamonioethylmetacrylatchloride).

In another preferred embodiment of the invention the coating-agent is a water-dispersion of the terpolymer from U.S. Pat. No. 4,557,925, consisting of 80–95% by weight of polyvinylchloride, 0.5–19% by weight of polyvinylacetate and 0.5–10% by weight of polyvinylalcohol.

In another preferred embodiment of the invention the coating polymer is a copolymer consisting of 50–100% by weight of polyvinylchloride and 0–50% by weight of polyvinylacetate.

The weight ratio, amount of pore-forming agent to total weight of the dry coating, depends on the chosen polymer and pore-former and the release pattern desired, but is normally between 40 and 95, preferably between 50 and 90 and most preferably between 55 and 88% by weight.

A plasticiser may be added to adjust the softening temperature (Tg) of the polymer. The Tg is an important factor for regulating the mechanical properties of the polymer. Examples of suitable plasticisers are acteyltributyl citrate, acetyltriethyl citrate, castor oil, diacetylated monbglycerides, dibutyl sebacate, diethyl phatalate, glycerin, mono- and diacetylated monoglycerides, polyethylene glycol, propylene glycol, triacetin, trietyl citrate.

The pore-forming agent in the coating suspension is preferably stabilized with one or more ionic, non-ionic or polymer surfactants. Examples of suitable surfactants are diethanolamine, fatty acids, HPMC (hyroxy propyl methyl cellulose), HPC (hydroxy propyl cellulose), monoethanolamine, nonoxynol, octoxynol, oleic acid, poloxamer, polyoxyethylene 50 stearate, polyoxyl fatty acid, polyoxyl hydrocarbon ether, polysorbate, povidone, salts of fatty acids, sodium lauryl sulfate, sorbitan ester, trolamine.

The aqueous dispersion of the polymer and the pore-forming agent may be used to coat solid cores, which in this context includes crystals, granules, pellets, tablets or the like.

The aqueous dispersion of the polymer and the pore-forming agent is preferably spray-coated onto the solid cores.

The obtained, coated cores may be cured with heat or moisture. Thus the coated preparation may be cured at a temperature higher than storage condition and at a humidity that could be specified for a period of time until the curing endpoint is reached. This endpoint is determined by comparing the dissolution profile with the profile from an accelerated storage condition, for example 3 months at 40° C. at ambient humidity. The curing may take place in the coating equipment or in a separate dryer as for example in a drying chamber or a drying vessel.

The drug in the solid core could for example be tranquillizers, antibiotics, hypnotics, antihypertensives, antianginics, analgesics, antiinflamatories, neuroleptics, antidiabetics, diuretics, antikolinergics, antihyperacidics, antiepileptics, ACE inhibitors, β-receptor antagonists and agonists, anaesthetics, anorexiants, antiarrythmics, antidepressants, anticoagulants, antidiarrhoetics, antihistamines, antimalariels, antineoplastics, immunosuppressives, antiparkinsonians, antipsychotics, antiplatelets, diuretics or antihyperlipidics.

The drug substance could for example be potassium chloride, theophylline, a theophylline salt, phenylpropanolamine, sodium salicylate, paracetamole, carbidopa, levodopa, diltiazem, enalapril, verapamil, naproxen, pseudoephedrin, nicorandil, oxybutuin, morphine, oxycodone or propranolol.

The aqueous suspension of pore-former and polymer can be diluted with an organic solvent up to 20%, preferably up to 10% and most preferably up to 5%. The organic solvent plasticises the polymer to enhance film formation. The organic solvent also decreases the solubility of the pore-former in the suspension. Thus by using a small amount of organic solvent some advantages may be obtained and, compared with the presently used system, the amount of organic solvent can be reduced. According to the preferred embodiment no organic solvent is included.

In its method aspect, the present invention is not limited by the drug or type of drug incorporated in the preparation. Any composition containing any presently known or future discovered orally acting drug may be coated in order to provide the highly advantageous controlled release pharmaceutical preparations of the present invention.

Furthermore, and to the best of our knowledge, the preparations per se including the preferred pore-forming agents mentioned above are not previously known or even suggested.

The invention is further illustrated by, but should not be limited to, the following preparations and example.

EXAMPLE

Core

The composition of the core is shown in table 1. The ingredients are granulated in a high shear mixer, dried and milled thereafter. The material is blended with lubricants and then compressed to tablets in a tablet press.

TABLE 1

| Ingredients | (mg/tablet) |
|---|---|
| Diltiazem hydrochloride | 350 |
| Sodium dihydrogen citrate | 218 |
| Povidone K25 | 42.4 |
| Magnesium stearate | 12.5 |
| Ethanol* | 45.4 |
| Total | 623 |

*Evaporates during the process

Coating Suspension

The composition of a coating is shown in table 2. The coating suspension was prepared by adding the polymer dispersion, the pore former (with a specific particle size of 25 µm) and deionised water to a final content of dry substances of 15% w/w, to a container with continuous stirring.

TABLE 2

| Ingredients | (%/coating) | Dry weight (mg) |
|---|---|---|
| Polymer dispersion-Polyvinylacetate (water dispersion) | 30 | 21 |
| Potassium bitartrate (KHT) | 70 | 49 |
| Deionised water* | | 397* |
| Total (mg) | | 70 |
| Total (mg/cm$^2$) | | 20 |

*Evaporates during the process

Coating

The cores were coated with the coating suspension in a coating pan. The coated tablets were allowed to dry in the pan for 15 minutes.

Different embodiments of the preparation according to the invention, shown in table 3, were made accordingly.

TABLE 3

| | | | Coating | | | |
|---|---|---|---|---|---|---|
| Batch | Core (Diltiazem) (mg) | Film weight (mg/cm$^2$) | Pore-former Type | (%) | Polymer Type | (%) |
| 1 | 350 | 20 | KHT[1] | 0 | PVAc[2] | 100 |
| 2 | 350 | 4.8 | KHT[1] | 0 | PVAc[2] | 100 |
| 3 | 350 | 20 | KHT[1] | 80 | PVAc[2] | 20 |
| 4 | 350 | 20 | KHT[1] | 60 | PVAc[2] | 40 |
| 5 | 320[3] | 24 | KHT[1] | 70 | P (EA-MMA)[4] | 30 |

[1]KHT = Potassium bitartrate
[2]PVAc = Polyvinylacetate
[3]100 mg of Polyethyleneoxid is included in the formulation
[4]P (EA-MMA) = Poly(ethylacrylate-methylmethacrylate) 2:1

Results

Table 4 shows results from an in vitro dissolution test (according to USP 23, paddle method) with the formulations from table 3.

Batch number 1 and 2 with no added pore-former have a very slow release pattern. The addition of pore-former (batch 3–5) increases the release rate and makes it possible to design formulations according to a desired release pattern.

Batch 2 and 4 had comparable drug-release rates. However, the polymer films from batch 2 ruptured during the analysis. Batch 4 showed much less variability in drug release compared to batch 2 and the polymer film still had good mechanical strength after the analysis.

TABLE 4

| Batch | Amount released Diltiazem (%) after x hours (pH 6,8) | | | | | | | Range at 40% released Diltiazem | |
|---|---|---|---|---|---|---|---|---|---|
| | 2 h | 4 h | 8 h | 12 h | 24 h | 48 h | 96 h | (%) | n |
| 1 | 0.1 | 0.1 | 0.1 | 0.1 | 0.1 | 0.1 | 0.6 | — | 6 |
| 2 | 3.7 | 7.0 | 14.9 | 22.2 | 41.7 | 89.4 | 101.3 | 17.7 | 3 |
| 3 | 26.8 | 50.8 | 81.6 | 93.2 | 97.0 | — | — | 2.2 | 6 |
| 4 | 0.6 | 1.5 | 8.5 | 19.7 | 41.2 | — | — | 3.5 | 6 |
| 5 | 15.0 | 35.1 | 65.1 | 89.3 | 101.4 | — | — | 7.2 | 6 |

After the 24 h in vitro dissolution test the tablet residuals (=the polymer films filled with water) were tested for mechanical strength (MS). The force required to crack the polymer film was recorded.

The following results were obtained.

TABLE 5

| Batch | 1 | 2 | 3 | 4 | 5 |
|---|---|---|---|---|---|
| MS (N) | — | 0 | 20 | 27 | 18 |

The same test performed on preparations according to the U.S. Pat. No. 5,472,612 demonstrated that the polymer films were broken with negligible forces i.e. forces well below 1 N.

The following tables show the effect of the particle size on the release rate.

TABLE 6

| | Coating | | Pore-former | | Coating Polymer |
|---|---|---|---|---|---|
| Batch | Core Diltiazem (mg) | Film Weight (mg/cm$^2$) | Type | Particle size (µm) | Amount (%) | P(EA-MMA) Amount (%) |
| A | 300 | 20 | KHT | 8 | 71 | 29 |
| B | 300 | 20 | KHT | 14 | 71 | 29 |

TABLE 7

| Batch | Amount released Diltiazem (%) after x h (pH 6.8) | | | | | Range at 40% released Diltiazem | |
|---|---|---|---|---|---|---|---|
| | 2 h | 4 h | 8 h | 12 h | 24 h | (%) | n |
| A | 11.4 | 31.6 | 62.1 | 82.4 | 96.9 | 5.4 | 6 |
| B | 1.8 | 14.3 | 36.8 | 54.1 | 85.8 | 4.4 | 6 |

EXAMPLE 2

The following example discloses the stability of the coating according to the present invention. Cores of Diltiazem, 300 mg, were prepared as previously described and divided into 2 groups. The cores of group 1 were coated with the polymer Eudragit® and the cores of group 2 were coated with the polymer Kollicoat®. Both coatings were prepared with 71% by weight of KHT according to the present invention. The tablets were stability tested for 6 months and the results are shown in the following table 8.

TABLE 8

| X hours | Initial amount | 3 months* | 3 months** | 6 months* | 6 months** |
|---|---|---|---|---|---|
| Eudragit, Amount (%) of released Diltiazem after x hours | | | | | |
| 2 | 7.3 | 9.4 | 8.0 | 8.3 | 8.5 |
| 4 | 25.5 | 28.6 | 27.2 | 27.4 | 27.9 |
| 8 | 53.3 | 58.8 | 58.1 | 57.7 | 59.4 |
| 12 | 74.1 | 79.3 | 79.6 | 78.8 | 81.2 |
| 24 | 97.4 | 95.6 | 96.0 | 96.4 | 96.2 |
| Kollicoat, Amount (%) of released Diltiazem after x hours | | | | | |
| 2 | 9.7 | 9.1 | 10.2 | 9.2 | 10.6 |
| 4 | 27.8 | 26.7 | 28.1 | 26.6 | 28.9 |
| 8 | 53.2 | 52.5 | 55.5 | 52.3 | 56.8 |
| 12 | 69.7 | 69.2 | 72.0 | 68.5 | 72.9 |
| 24 | 89.4 | 88.7 | 89.6 | 87.4 | 89.8 |

*25° C./75% RH
**40° C. ambient humidity

As can be seen both groups demonstrated excellent stabilty properties even in such severe conditions as 6 months in 40° C.

What is claimed is:

1. A method for producing a controlled-release pharmaceutical preparation with a particle-containing coating comprising the steps of:
   a) preparing a drug-containing solid core;
   b) suspending a pore-forming agent having a balanced solubility in an aqueous dispersion of a film-forming, essentially water insoluble polymer in order to form a coating suspension having a predetermined amount of solid particles of the pore-forming agent suspended therein
   c) coating the solid core with the obtained suspension; and
   d) drying the coating;
   wherein the pore-forming agent is soluble in body fluids;
   wherein the mean particle size of the pore-forming agent is 0.5–100 μm; and
   wherein the amount of the pore-forming agent is 40–95% by weight of the total weight of the dry coating and;
   wherein the coating provides good mechanical strength requiring a force of from 18N to 27N to break, compared to a force below 1N.

2. A method according to claim 1, wherein the solubility of the pore-forming agent is below 30 mg/ml in the aqueous coating dispersion.

3. A method according claim 1, wherein the mean particle size of the pore-forming agent is 1–25 μm.

4. A method according to claim 1, wherein the pore-forming agent is selected from a group consisting of potassium salts, calcium salts, magnesium salts, amino acids, weak acids, carbohydrates, polymers with amino and/or acid functions or a composition wherein at least one of the components is selected from one of these groups.

5. A method according to claim 1, wherein the pore-forming agent is potassium bitartrate, creatine, aspargine, glutamine, aspartic acid, glutamic acid, leucin, neroleucine, inosine, isoleucine, magnesium citrate, magnesium phosphate, magnesium carbonate, magnesium hydroxide, magnesium oxide or a composition wherein at least one component is selected from one of these substances.

6. A method according to claim 1, wherein the pore-forming agent is chitosan and poly(butyl methacrylate, (2-dimethyl aminoethyl) methacrylate, methyl methacrylate) 1:2:1.

7. A method according to claim 1, wherein the water insoluble polymer is selected from one of the groups of cellulose esters, acrylic polymers, polyvinyl acetates, polyvinyl chlorides or a composition wherein at least one component is selected from one of the groups.

8. A method according to claim 1, wherein the coating polymer is ethylcellulose, celluloseacetate, celluloseacetatebutyrate, celluloseacetatepropionate, nitrocellulose, polymethylmethacrylate, poly(ethylacrylate, methylmethacrylate), polyvinylacetate, polyvlnyichioride, polyethylene, polyisobutylene, poly(ethylacrylate, methylmethacrylate, trimethylamonioethylmethacrylate chloride), a block- or copolymer of the polymers or a composition wherein at least one of the components is selected from these polymers.

9. A method according to claim 1, wherein the coating polymer is a copolymer consisting of 50–100% by weight of polyvinyl chloride and 0–50% by weight of polyvinyl acetate.

10. A method according to claim 1, wherein the coating polymer is a copolymer consisting of 80–95% by weight of polyvinylchloride, 0.5–19% by weight of polyvinylacetate and 0.5–10% by weight of polyvinylalcohol.

11. A method according to claim 1, wherein the solid core includes at least one drug selected from the group consisting of tranquillizers, antibiotics, hypnotics, antihypertensives, antianginas, analgesics, anti-inflamatories neuroleptics, antidiabetics, diuretics, anticholinergics, antihyperacidics or antiepileptics, ACE inhibitors, β-receptor antagonists and agonists, anaesthetics, anorexiants, antiarrythmics, antidepressants, anticoagulants, antidiarrheals, antihistaines, antimalariels, antineoplastics, immunosuppressives, antiparkinsonians, antipsychotics, antiplatelets, diuretics, antihyperlipidics.

12. A method according to claim 1, wherein the drug for the solid core is potassium chloride, theophylline, a theophylline salt, phenylpropanolamine, sodium salicylate, choline theophyllinate, paracetamole, carbidopa, levodopa, diltiazem, enalapril, verapamil, naproxen, pseudoephedrine nicorandil, oxybutyin, morphine, oxycodone or propranolol.

13. A method according to claim 1, wherein the aqueous dispersion includes at most 20% by weight of organic solvent.

14. A method according to claim 1, wherein the obtained coated cores are cured with heat or moisture.

15. A method according to claim 1, wherein the pore-former in the coating suspension is stabilized with one or more ionic, non-ionic or polymer surfactants.

16. A method according to claim 1, wherein the coating polymer is plasticized.

17. A controlled-release pharmaceutical preparation comprising:
   a drug-containing solid core; and
   a coating on the solid core, said coating having a water insoluble polymer with a predetermined amount of particles of a pore-forming agent dispersed therein, said pore-forming agent having a balanced solubility in an aqueous dispersion of a film-forming, essentially water insoluble polymer
   wherein the mean particle size of the pore-forming agent is 0.5–100 μm; and
   wherein the amount of the pore-forming agent is 40–95% by weight of the total weight of the dry coating and;
   wherein the coating provides good mechanical strength requiring a force of from 18N to 27N to break, compared to a force below 1N.

18. A controlled-release pharmaceutical preparation according to claim 17, wherein the pore-forming agent is a member selected from the group consisting of: potassium bitartrate, creatine, aspartic acid, glutamic acid, inosine, aspargine, glutamine leucin, neroleucine, isoleucine, magnesium phosphate, magnesium carbonate, magnesium hydroxide, chitosan and poly (butyl methacrylate, (2-dimethyl aminoethyl) methacrylate, methyl methacrylate) 1:2:1 or a composition wherein at least one component is selected from one of these substances.

19. A controlled-release pharmaceutical preparation according to claim 17, wherein the amount of the pore-forming agent is 50–90% by weight of the total weight of the dry coating.

20. A controlled-release pharmaceutical preparation according to claim 17, wherein the polymer is ethylcellulose, celluloseacetate, celluloseacetatebutyrate, celluloseacetatepropionate, nitrocellulose, polymethylmethacrylate, poly(ethylacrylate, methylmethacrylate), polyvinylacetate, polyvinylchloride, polyethylene, polyisobutylene, poly(ethylacrylate, methylmethacrylate, trimethylamonioethyl methacrylate chloride), a block- or copolymer of the polymers or a composition wherein at least one of the components is selected from these polymers.

21. A controlled-release pharmaceutical preparation according to claim 17, wherein the coating polymer is a copolymer consisting of 50–100% by weight of polyvinyl chloride and 0–50% by weight of polyvinyl acetate.

22. A controlled-release pharmaceutical preparation according to claim 17, wherein the coating polymer is a copolymer consisting of 80–95% by weight of polyvinylchloride, 0.5–19% by weight of polyvinylacetate and 0.5–10% by weight of polyvinylalcohol.

23. A controlled-release pharmaceutical preparation according to claim 17, wherein the amount of pore-forming agent is 55–88% by weight of the total weight of the dry coating.

* * * * *